United States Patent [19]

Milligan et al.

[11] 3,957,889

[45] May 18, 1976

[54] SELECTIVE NITRATION OF AROMATIC AND SUBSTITUTED AROMATIC COMPOSITIONS

[75] Inventors: Barton Milligan, Ardmore; Donald G. Miller, Boothwyn, both of Pa.

[73] Assignee: Air Products and Chemicals, Inc., Allentown, Pa.

[22] Filed: May 2, 1975

[21] Appl. No.: 574,131

[52] U.S. Cl. .......................... 260/645; 260/612 D; 260/646
[51] Int. Cl.² ................. C07C 79/10; C07C 79/12
[58] Field of Search ................ 260/612 D, 645, 646

[56] References Cited
UNITED STATES PATENTS

| | | | |
|---|---|---|---|
| 2,948,759 | 8/1960 | Wright | 260/645 X |
| 3,126,417 | 3/1964 | Tsang | 260/645 |
| 3,196,186 | 7/1965 | Sogn et al. | 260/645 |
| 3,708,546 | 1/1973 | Coon et al. | 260/645 |

FOREIGN PATENTS OR APPLICATIONS 1,333,360   10/1973   United Kingdom

*Primary Examiner*—Leland A. Sebastian
*Attorney, Agent, or Firm*—Russell Brewer; Barry Moyerman

[57] ABSTRACT

This invention relates to an improvement in a process for nitrating an aromatic or substituted aromatic compound e.g., toluene or ortho-xylene, by reacting such aromatic or substituted aromatic in the presence of nitric acid. The improvement for enhancing the rate of nitration as well as the selectivity of nitration at the para-position in this process comprises carrying out the nitration reaction in the presence of at least an effective amount of anhydrous calcium sulfate or soluble anhydrite.

8 Claims, No Drawings

SELECTIVE NITRATION OF AROMATIC AND SUBSTITUTED AROMATIC COMPOSITIONS

BACKGROUND OF THE INVENTION

It has long been known to nitrate aromatic and substituted aromatic compositions for producing a variety of products which are useful as intermediates in the chemical industry. For example, toluene is nitrated to form an intermediate, i.e., paranitrotoluene, which is useful for the preparation of dyestuffs and drugs intermediates. A dinitrotoluene, a mixture of 2, 4 and 2,6-dinitrotoluene has been employed in the manufacture of toluene diisocyanate which is useful for the formation of polyurethanes.

It is known that in the nitration of mono-substituted aromatic compositions that 3 isomers can be formed and the proportion of each isomer formed often is largely dependent upon the functional group present on the aromatic ring. For example, when toluene is nitrated, approximately 58% of the ortho-isomer, 38% of the para-isomer and 4% of the metaisomer are formed whereas when chlorobenzene is nitrated about 30% of the product is the ortho-isomer and 70% is the para-isomer. Even though specific groups on the aromatic ring can assist in the formation of a larger proportion of appropriate isomers, these groups may not be desired in the final product or they may not provide sufficient selectivity.

The presence of a plurality of isomers in the nitration mixture may be undesirable and can lead to economic waste in terms of the materials consumed and in terms of recovery or disposal. For example, with respect to nitrotoluene, paranitrotoluene is useful, while the ortho and meta-nitrotoluene isomers are not as useful, in the preparation of dyestuffs and drug intermediates. Thus, these isomers must be removed from the product which adds to the cost.

For end uses in the polyurethane industry a high ratio of 2, 4-dinitrotoluene to 2, 6-dinitrotoluene is desired. Some 2, 6-isomer of dinitrotoluene is produced by nitrating orthonitrotoluene whereas solely the 2, 4-dinitrotoluene isomer is produced from para-nitrotoluene which again shows the importance of obtaining para-nitrotoluene. The isomers produced from meta-nitrotoluene are unacceptable in many of the polyurethane applications and thereby represent a problem in terms of purification, i.e., removal of the meta-nitrotoluene from the product.

Another substituted aromatic compound, i.e., 4-nitro ortho-xylene is highly useful and desirable in many applications in the chemical industry. When orthoxylene is conventionally nitrated, approximately equal amounts of 4-nitro ortho-xylene and 3-nitro ortho-xylene are formed. The 3-nitro isomer generally is removed from the product which adds to the cost and leads to waste.

DESCRIPTION OF THE PRIOR ART

For a considerable time practitioners in the art of nitration have sought methods for not only enhancing the rate of nitration of aromatic and substituted aromatic composition, but the selectivity of nitration, e.g., the para position, on the aromatic molecule.

Many catalysts or promoters have been developed and used for enhancing the nitration reaction but many did not enhance the selectivity of nitration. Cataylsts or promoters are required for achieving a rate of nitration acceptable for commercial production. These rates cannot be attained simply by increasing the concentration of the reactants.

In a conventional method of nitration of an aromatic or a substituted aromatic compound, nitric acid is mixed with concentrated sulfuric acid and added in liquid phase to the aromatic composition. The sulfuric acid is added to the nitric acid to permit formation of nitronium ions which can attack the aromatic ring for effecting nitration thereby catalyzing the reaction. As the reaction proceeds water is formed and dilutes the sulfuric acid. Accordingly, the sulfuric acid must be replenished to bring it to an acceptable concentration for catalyzing the reaction.

Aromatic sulfonic acids have been used to promote selectivity of niration, particularly at the para position in the nitration of toluene. The aromatic sulfonic acids can be in molecular form or they can be attached to a polymer network i.e., an ion exchange resin. These aromatic sulfonic acids, although suited for enhancing selectivity of the nitration of toluene, suffer from certain disadvantages. They are often difficult to regenerate and the sulfonic acids have very little capacity in terms of the sulfonic acid required per part of product produced before regeneration is required. An unsupported sulfonic acid presents problems in that it frequently is soluble in the product and makes separation more difficult.

Another approach suggested for enhancing selectivity of nitration at the para position in toluene is through the use of nitrate esters of highly hindered alcohols. The basic problems with this method are (a) the carrier is quite costly, (b) there are difficulties in regenerating the alcohol after nitration, and (c) there is the possibility of losing the carrier alcohol by rearrangement under the acid conditions necessary for nitration.

Another variation in the conventional nitration process has been suggested which employs lower temperatures and stronger nitric acid mixtures than are customarily employed for nitration. This is particularly true for toluene. The problem with this technique is that it results in the formation of a large proportion of dinitrotoluene as well as mononitrotoluene. Even though a large proportion of the desired isomer is formed, the reaction medium is not well suited for the synthesis of the mono nitrotoluene.

SUMMARY OF THE INVENTION

This invention relates to an improvement in a process for nitrating an aromatic or substituted aromatic composition wherein nitric acid is contacted with the composition under conditions for effecting nitration thereof. The improvement for enhancing the rate of nitration as well as the selectivity of the nitration comprises carrying out said nitration in the presence of at least an effective amount of soluble anhydrite for increasing the nitration or the selectivity of the nitration.

Advantages of this process include:
a. The ability to carry out the nitration at moderate temperatures, e.g., room temperature (25° C.) at enhanced reaction rates as compared to non-catalyzed nitration methods;
b. The ability to enhance the selectivity of the nitration particularly in the alkyl aromatic compositions, e.g., toluene at the para position; and
c. The use of a relatively cheap promoter or catalyst which can be recovered and regenerated easily for subsequent use.

DESCRIPTION OF THE PREFERRED EMBODIMENT

Broadly, the aromatic and substituted aromatic compositions typically suited for nitration and practicing this invention are represented by the formula: $RC_6H_4R_1$ wherein R is a lower alkyl radical having from 1–4 carbon atoms, halogen, haloalkyl, nitro, or —$OCH_3$ group and $R_1$ is a lower alkyl radical having from 1–4 carbon atoms, halogen, nitro, or hydrogen group preferably hydrogen. Of these compositions the lower alkyl aromatic, polyalkylaromatic, and the halo alkyl aromatic compositions are best suited for practicing the invention. The nitration reaction products of these compositions have wide usage in the chemical industry, and thus enhanced nitration rates or selectivity of the nitration at the para position or both may be important.

The aromatic ring can be substituted as shown in the formula, with a wide variety of groups. These groups should be sufficiently inert to the nitration reaction so that they do not substantially interfere with the nitration of the aromatic ring. Common aromatic and substituted aromatic compositions contemplated for practicing this invention are toluene, ortho-xylene, n-propyl benzene, isopropyl benzene, t-butylbenzene, n-butyl benzene, ortho-chlorotoluene, ethyl benzene, ortho-nitrotoluene, meta-xylene, benzene, and nitrobenzene.

The catalyst or promoter employed in the practice of this invention and used for enhancing the rate of nitration or the selectivity of nitration at the para position or both is anhydrous calcium sulfate or soluble anhydrite as it is sometimes called. Soluble anhydrite is made by heating gypsum, $CaSO_4.2H_2O$ which is dried, crushed, sized and heated to about 450° to 500°F for 2 hours. The resulting product is a soluble, granular, porous product having sufficient mechanical strength to support its own weight. Soluble anhydrite readily takes on water, in moist air to form calcium sulfate hemi-hydrate, $CaSO_4.\frac{1}{2}H_2O$ and has been used as a dessicant and sold under the trademark "Drierite."

The Drierite catalyst is added to the reaction medium in a proportion at least sufficient to increase the rate of nitration or to influence the selectivity of the nitration or both. However, proportions of this magnitude generally are not sufficient for achieving preferred results for enhancing selectivity of the nitration, particularly with toluene, or forming the para isomer. Generally, at least 25% of the stoichiometric amount required for nitration, based on the theoretical quantity of nitrated product, is added to the reaction medium and this proportion can be increased to at least 500% in excess of the theoretical stoichiometric amount based on the nitrated product. Preferably the proportion of soluble anhydrite which is added to the nitration reaction is at least the theoretical stoichometric requirement. When less than 25% of the stoichometric quantity of soluble anhydrite is employed, then the advantages, in terms of rate of reaction or selectivity of nitration at the para position, may be reduced. As the proportion of soluble anhydrite is increased above 25% to the stoichiometric requirement, then enhanced rate and selectivity advantages are noticed. When the proportion of soluble anhydrite is increased above the theoretical stoichiometric requirement, then disadvantages appear. These disadvantages include increased cost of material, in terms of the magnitude of the material to be removed and regenerated. Preferably at least a stoichometric amount to about 100% in excess of soluble anhydrite is used.

The stoichiometric quantity of soluble anhydrite to be used for the nitration (assuming anhydrous conditions) is determined in this way. One mole of water is produced for each mole of mononitrated aromatic or substituted aromatic compound produced. 1 mole of soluble anhydrite can absorb ½ mole water. Thus, the stoichiometric quantity requires that two moles of soluble anhydrite be employed for each mole of mononitrated aromatic or substituted aromatic composition produced. If the dinitrated aromatic or substituted aromatic composition is desired, then stoichiometrically four moles soluble anhydrite are required to absorb the 2 moles water generated by the dinitration reaction. For convenience, the reference point (assuming anhydrous nitric acid is employed) used is the theoretical quantity of water that would be produced if all of the nitric acid reacted. Otherwise the amount of soluble anhydrite must be increased to compensate for water in the nitric acid as diluent.

Although not intending to be bound by theory, it is believed that the soluble anhydrite, because of its tremendous affinity for water, removes water from the nitric acid to form nitronium ions. These nitronium ions can attack the aromatic ring to effect nitration. On the other hand, other dessicants, e.g., silica gel and plaster of paris have not resulted in enhancing the rate of nitation to the extent obtained by the use of soluble anhydrite nor do they enhance nitration at the para position in toluene.

Calcium sulfate hemi-hydrate which is formed by the soluble anhydrite absorbing one-half mole water can be regenerated into the soluble anhydrite form by conventional techniques. Typically, the calcium sulfate hemi-hydrate is heated to 400° to 425°F. with a stream of hot air. One of the advantages of soluble anhydrite in practicing this invention is that it can be used many times before it must be discarded to waste.

The reaction conditions suited for effecting nitration of this invention generally are the same as those conventionally used in the past except for the addition of soluble anhydrite. For example, temperatures as low as 0° C. and up to about 125° C. can be employed. Through experimentation it has been found that the proportion of the para isomer produced, in the case of toluene, is lower when made at higher temperatures e.g., 100° C. than the proportion produced at lower temperatures e.g., 25° C. However, the proportion of para-isomer formed at higher temperatures is greater where the soluble anhydrite is included in the reaction medium than the proportion of para-isomer produced at the same temperature by conventional techniques. Pressure suited for practicing this invention can vary from subatmospheric to superatmospheric although atmospheric pressures are preferred for reasons of efficiency and economy.

Because Drierite or soluble anhydrite absorbs only 6.6% of its weight of water, the large scale reaction of toluene and nitric acid in stoichiometric ratio generally requires the use of a diluent to provide a tractable reaction mixture. Compounds such as chloroform methylene chloride, nitrotoluene, and the like can be used. Preferably the reactants should be highly soluble in the diluent in order to achieve preferred results. Diluents which are not solvents for the reactants tend to reduce the rate and selectivity of the nitration. The diluent can have an effect on the rate of nitration and selectivity, but the results typically are better than conventional nitration techniques. For example, chloroform results in lower ortho-para ratios than methylene chloride, but both give lower ratios than are obtained in conventional nitration.

Using the reaction conditions above, the nitration can be carried out preferably with conventional reactants for nitration. Typically, nitric acid in a concentration of from 30 to 100% is used as the nitrating agent. Preferably anhydrous nitric acid is employed as this reduces the amount of water in the system. Nitric acid can also be generated in situ by employing an alkali metal nitrate and an acid e.g., sulfuric.

The following examples are provided to illustrate preferred embodiments of this invention and are not intended to restrict the scope thereof. All percentages are expressed as weight percentages and all temperatures are in degrees centigrade.

EXAMPLE 1

A 60 ml portion of toluene was treated with an 80 ml portion of a mixed acid consisting of 34 mole percent concentrated sulfuric and 8 mole percent concentrated nitric acid. Treatment was effected by spraying the acid through the toluene from a syringe. The temperature of the reaction was maintained at about 25° C.

A sample of the toluene so treated was taken and divided into two parts. Sample I was the control. To Sample II was added 0.23 grams soluble anhydrite (Drierite) per milliliter of reaction medium. At the end of 1 hour the samples were analyzed by gas chromotography and also at the end of a 24 hour period. The analyses showed the composition of both the control and experimental samples to be about the same at the end of 24 hours as at the end of one hour, thus showing most of the reaction was completed in one hour. The compositions below represent the analyses of the Samples I and II at the end of the 1 hour period.

TABLE I

|  | Untreated mole % in sample (balance toluene) | 100% Isomer Corrected to 100% MNT | mole % in sample (balance toluene) | 100% Isomer Corrected to 100% MNT |
|---|---|---|---|---|
|  | SAMPLE I | SAMPLE I | SAMPLE II | SAMPLE II |
| ortho | 0.373% | 52.2% | 1.197% | 41.5% |
| meta | 0.025 | 3.9 | 0.070 | 2.4 |
| para | 0.243 | 37.9 | 1.616 | 56.1 |
| Total MNT | .641% |  | 2.883% |  |
| Ratio ortho/para | 1.53 |  | 0.74 |  |

The results show that Sample 1, which was the control sample, resulted in a production of only 0.641 mole percent mononitrotoluene whereas the treated sample containing the soluble anhydrite resulted in producing 2.883 mole percent mononitrotoluene. These results show that the addition of soluble anhydrite to the reaction medium enhanced the rate and the extent of nitration. The results also bear out the fact that the percent of the desired para-isomer formed after addition of the soluble anhydrite increased substantially. The ratio of ortho to para-isomer in Sample 2 was approximately 0.74 . Conventional nitration reactions involving toluene as exemplified by Sample I have a ratio of approximately 1.5 to 1.8 ortho to para-isomer. Thus, the results show that soluble anhydrite is effective for enhancing the selectivity or increasing the proportion of para-isomer formed during the nitration reaction of toluene.

EXAMPLE II

A 100 gram portion of the powdered, soluble anhydrite (Drierite) was added to 100 milliliters toluene and mixed therein. A 13.6 gram portion of anhydrous nitric acid was added to the mixture of toluene and soluble anhydrite drop by drop over a 30 minute period. After all of the nitric acid was added to the toluene-soluble anhydrite mixture, the reaction was permitted to continue for 3 hours at 25° C. Then 26 grams nitrobenzene was added to the reaction medium and the medium was stirred for an additional 30 minutes. The reaction medium then was filtered and the filtrate was analyzed by gas chromatography using the added nitrobenzene as the internal standard. Results showed that a yield of 89% mononitrotoluene, based on the nitric acid, was obtained.

Assuming that all of the nitric acid would react to form the mononitrotoluene product, it follows that 0.215 mole water would be produced. The quantity of soluble anhydrite added to the reaction medium was approximately 70% in excess of the theoretical stoichiometric quantity required for absorbing all the water that would be generated by the reaction. As it turned out, the quantity of soluble anhydrite, based on the water produced by the actual nitration, was 90% in excess of the stoichiometric quantity required for absorbing the actual water generated.

The mononitrotoluene composition produced above analyzed as follows: 43.2% ortho-nitrotoluene, 2.3% meta-nitrotoluene and 54.4% para nitrotoluene. The ratio of ortho to para isomer formed was 0.78 or about one-half of that obtained by conventional nitration techniques. It should also be noted that the quantity of meta-isomer formed was about one-half of that ordinarily formed by conventional nitration techniques.

Thus the results show that the addition of soluble anhydrite to the reaction medium not only gave good yield in terms of the nitrotoluene produced, based on the nitric acid employed, but in terms of an increased proportion of the desired para isomer at the expense of the less desirable ortho and metaisomers.

EXAMPLE III

An 86 gram portion of soluble anhydrite regenerated from Example II by first heating in a vacuum at 100°C for 7 hours for removal of organic material and then over night at 200°C. was added to a 100 milliliter portion of toluene. This mixture was heated to 45°C. and stirred while an 18.1 gram portion of anhydrous nitric acid was added drop by drop over a 30-minute period. Agitation was continued for 1 ½ hours, then a 26 gram portion of nitrobenzene was added to the reaction mixture and stirring was continued for an additional hour. After this one hour period, the reaction mixture was filtered and the filtrate analyzed by gas chromotography using the nitrobenzene as the internal standard. A yield of 61% mononitrotoluene was obtained based on the nitric acid charged. The mononitrotoluene had the following composition: 44.1% ortho-nitrotoluene, 2.8% meta-nitrotoluene, and 53.1% paranitrotoluene. Thus the results show a substantial increase in the proportion of para-isomer was obtained by the addition of the soluble anhydrite to the reaction medium.

Assuming that all the nitric acid is converted to mononitrotoluene, the quantity of soluble anhydrite added to the reaction medium was about 12% in excess of the theoretical stoichiometric quantity required for absorbing all of the water that would be generated. In actual practice, the quantity of soluble anhydrite added was about 80% in excess of the theoretical stoichiometric quantity necessary for absorbing the actual water generated.

EXAMPLE IV

A 100g portion of soluble anhydrite was added to a solution of 32.9g toluene in 100 ml chloroform. Then a 22.6g portion of anhydrous nitric acid was added to the dispersion over a 30-minute period. Stirring at 25°C was continued for an additional 2 ½ hour period. Nitrobenzene was added before the last half hour period and was used as the internal standard. Gas chromatographic analysis showed a 93.2% yield of nitrotoluene with the proportion being 49.1% ortho, 2.1% meta, and 48.8% para.

EXAMPLE V

The procedures of Example II and Example III where noted were followed except that various compositions and reaction times as set forth in Table 2 were employed. The reactions were carried out at approximately 25°C. the quantity of soluble anhydrite employed was about 70% in excess of the theoretical stoichiometric quantity necessary for absorbing the water generated.

The procedure of Example II was followed except that a similar quantity of plaster of paris ($CaSO_4 \cdot \frac{1}{2} H_2O$) based on stoichiometric proportions was added to one sample and a similar quantity of silica gel based on stoichiometric proportions was added to another sample in place of the soluble anhydrite. The yield of mononitrotoluene, based on the nitric acid charged, at the end of a two hour period was small in the case of plaster of paris. The ratio of ortho-nitrotoluene to para-nitrotoluene isomer was 1.31. With respect to the sample employing the silica gel, the yield of mononitrotoluene, based on the nitric acid charged, over a 16 hour reaction period was 48%. The ratio of ortho-nitrotoluene to para-nitrotoluene isomer was 1.21.

These results show that silica gel and plaster of paris, even though commonly used dessicants, are not as effective as soluble anhydrite for enhancing the selectivity or the extent of the nitration reaction. Poorer nitration rates are manifest from the low yields obtained based on the nitric acid charged even though similar reaction times were employed. The results also show that the quantity of para-nitrotoluene isomer produced is substantially less than is produced when soluble anhydrite is employed. The ratios of the orthonitrotoluene to para-nitrotoluene, with both the plaster of paris and silica gel, are about the same as obtained by conventional nitration techniques.

EXAMPLE VI

The procedure of Example II was followed except that 100 grams of macroreticular sulfonated polystyrene resin which is known and used as a catalyst, and sold under the trade name Amberlyst-15 was substituted for soluble anhydrite. The reaction time was increased to 6 hours. The yield of mononitrotoluene produced, based on the nitric acid charged, was 46%. The isomer distribution was as follows: 43.4% ortho-nitrotoluene, 3.1% meta-nitroluene, and 53.5% para-nitrotoluene.

Although the isomer distribution obtained by employing the sulfonated polystyrene resin was similar to that obtained by using soluble anhydrite, the yield of

TABLE 2

| Composition | Time | Yield (based on HNO$_3$) | Isomer Distribution | |
|---|---|---|---|---|
| o-xylene | 16 hrs | 39% | 3-nitro-o-xylene | 32% |
| | | | 4-nitro-o-xylene | 68% |
| m-xylene | 5 hrs | 62% | 2-nitro-m-xylene | 7.9% |
| | | | 4-nitro-m-xylene | 92.1% |
| chlorobenzene | 16 hrs | 87% | o-nitrochlorobenzene | 24% |
| | | | p-nitrochlorobenzene | 76% |
| o-nitrotoluene* | 16 hrs | ** | 2,4-dinitrotoluene | 69% |
| | | | 2,6-dinitrotoluene | 31% |
| benzene | 3½ hrs | 42% | nitrobenzene | |

*Procedure analogous to Example IV.
**Not determined.

The results show that the soluble anhydrite was effective for selectively nitrating at the para position. For example, greater quantities of 4-nitro-ortho-xylene and 4-nitro-meta-xylene were obtained with ortho-xylene and meta-xylene by using the soluble anhydrite than were obtained by conventional nitration. Furthermore, nitration of chlorobenzene to the para isomer is enhanced and ortho-nitrotoluene yields enhanced selectivity to the 2–4-isomer. The results also show the ability of the soluble anhydrite for activating compositions of low reactivity e.g., chlorobenzene and ortho-nitrotoluene.

mononitrotoluene produced was much lower than was obtained with the soluble anhydrite. The yield of mononitrotoluene suggests that the sulfonated polystyrene resin catalyst is either less active than the soluble anhydrite in influencing or enhancing the rate of nitration or it has a smaller capacity. If the latter is true, then larger quantities of sulfonated polystyrene resin are necessary.

What is claimed is:

1. In a process for nitrating an aromatic or substituted aromatic composition, wherein nitric acid is contacted with said composition under conditions for effecting nitration thereof, the improvement for enhancing the rate of nitration and the selectivity of the nitration which comprises: carrying out said nitration in the presence of at least an effective amount of soluble anhydrite for selectively enhancing the rate or selectivity of nitration.

2. The process of claim 1 wherein the amount of soluble anhydrite employed in said nitration is at least about 25% of the theoretical stoichiometric amount to about 500% in excess of the theoretical stoichiometric amount based on the moles of water capable of being generated by the nitration reaction and present as diluent.

3. The process of claim 2 wherein the soluble anhydrite is added in a proportion of from about the theoretical amount and to an amount not exceeding about 100% in excess of the stoichiometric amount.

4. The process of claim 3 wherein said composition is an alkyl aromatic composition having from 1–4 carbons in the alkyl group.

5. The process of claim 4 wherein said composition is toluene.

6. The process of claim 3 wherein said composition is a polyalkyl aromatic composition having from 1–2 carbon atoms per alkyl group.

7. The process of claim 6 wherein said polyalkyl composition is xylene.

8. The process of claim 3 wherein said composition is chlorobenzene.

* * * * *